US006399764B1

(12) United States Patent
Riley

(10) Patent No.: US 6,399,764 B1
(45) Date of Patent: Jun. 4, 2002

(54) **DNA MOLECULE ENCODING FOR CELLULAR UPTAKE OF *MYCOBACTERIUM TUBERCULOSIS* AND USES THEREOF**

(75) Inventor: Lee W. Riley, Berkeley, CA (US)

(73) Assignee: Cornell Research Foundation, Inc, Ithaca, NY (US)

( * ) Notice: Subject to any disclaimer, the term of this patent is extended or adjusted under 35 U.S.C. 154(b) by 0 days.

(21) Appl. No.: 09/574,462

(22) Filed: May 18, 2000

Related U.S. Application Data

(62) Division of application No. 08/907,229, filed on Aug. 6, 1997, now Pat. No. 6,072,048.
(60) Provisional application No. 60/040,097, filed on Mar. 10, 1997.

(51) Int. Cl.[7] .................. C07H 21/04; A61K 39/04; A61K 39/02; A61K 38/00; C07K 1/00
(52) U.S. Cl. .................. 536/23.7; 424/93.4; 424/190.1; 424/192.1; 424/248.1; 435/7.24; 530/300; 530/350; 536/22.1; 536/23.1; 536/24.32
(58) Field of Search .................. 424/190.1, 192.01, 424/93.4, 248.1; 435/7.24; 530/350, 300; 536/22.1, 23.1, 23.7, 24.32

(56) References Cited

U.S. PATENT DOCUMENTS

| | | |
|---|---|---|
| 5,108,745 A | 4/1992 | Horwitz |
| 5,183,737 A | 2/1993 | Crawford et al. |
| 5,239,066 A | 8/1993 | Falkow et al. |
| 5,478,726 A | 12/1995 | Shinnick et al. |

FOREIGN PATENT DOCUMENTS

| | | |
|---|---|---|
| EP | WO 95/06726 | 3/1995 |
| EP | WO 96/26275 | 8/1996 |

OTHER PUBLICATIONS

R.R. Isberg, et al., "A single genetic locus encoded by *Yersinia Pseudotuberculosis* permits invasion of cultured animal cells by *Escherichia coli* K–12", *Nature* 317:262–64 (1985).
B. Bloom et al., "Tuberculosis: Commentary on a Reemergent Killer," *Science*, 257:1055–64 (1992).
"Control of Tuberculosis in the United States," *American Thoracic Society*, 146:1623–33 (1992).
F. Laraque et al., "Tuberculosis in HIV–Infected Patients," *The AIDS Reader* (Sep./Oct. 1992).
City Health Information, vol. 11 No. 5 (1992).
Arruda et al., "Cloning of an *M. tuberculosis* DNA Fragment Associated with Entry and Survival Inside Cells," *Science* 261:1454–1457 (1993).
Arruda et al., "Cloning of a *Mycobacterium tuberculosis* Gene Necessary for Invasion of Cultured Epithelial Cells," *Abstracts of the General Meeting* 92:41 (1992).
Horwitz et al., "Protective Immunity Against Tuberculosis Induced by Vaccination With Major Extracellular Proteins of *Mycobacterium tuberculosis*," *Proc. Natl. Acad. Sci. USA* 92:1530–34 (1995).
Daniel, "Soluble Mycobacterial Antigens," *The Mycobacteria: A Sourcebook* pp. 417–465 (1984).
Crowle, "Immunization Against Tuberculosis: What Kind of Vaccine?," *Infection and Immunity* 56(11):2769–2773 (1988).
Griffin et al., "Animal Models of Protective Immunity in Tuberculosis to Evaluate Candidate Vaccines," *Trends in Microbiology* 3(11):418–423 (1995).
Kuo et al., "Novel Systems for Controlled Delivery of Macromolecules," The Johns Hopkins University, abstract, *Critical Review in Eukaryotic Gene Expression* 661:59–73 (1996).
Riley, Direct Submission, GenBank Database Document Accession No. X70901 (Jan. 28, 1993)(Sep. 19, 1996).
Ledley, "Nonviral Gene Therapy: The Promise of Genes as Pharmaceutical Products," *Human Gene Therapy* 6:1129–1144 (1995).
Chitale et al., "Isolation and Characterization of a Recombinant *Mycobacterium tuberculosis* Protein Involved in Mammalian Cell Centry," Cornell University Medical College, abstract XP 002046900 U–119 (1995).

*Primary Examiner*—Rodney P Swartz
(74) *Attorney, Agent, or Firm*—Nixon Peabody LLP

(57) ABSTRACT

The present invention relates to DNA molecules associated with conferring on *Mycobacterium tuberculosis* an ability to enter mammalian cells. The protein encoded by these DNA molecules are useful in vaccines to prevent infection by *Mycobacterium tuberculosis*, while the antibodies raised against this protein can be employed in passively immunizing those already infected by the organism. Both these proteins and antibodies may be utilized in diagnostic assays to detect *Mycobacterium tuberculosis* in tissue or bodily fluids. The protein of the present invention can be associated with various other therapeutic materials, for administration to mammals, particularly humans, to achieve uptake of those materials by such cells.

9 Claims, 6 Drawing Sheets

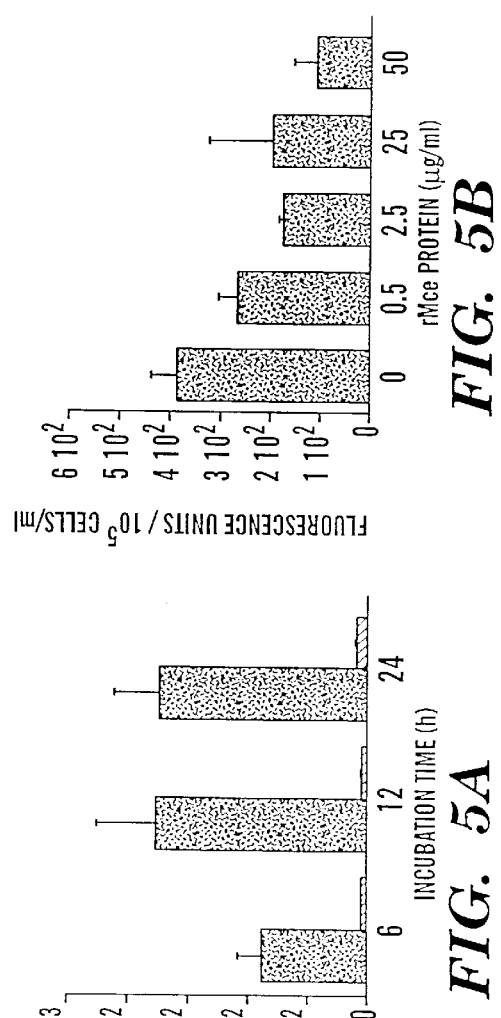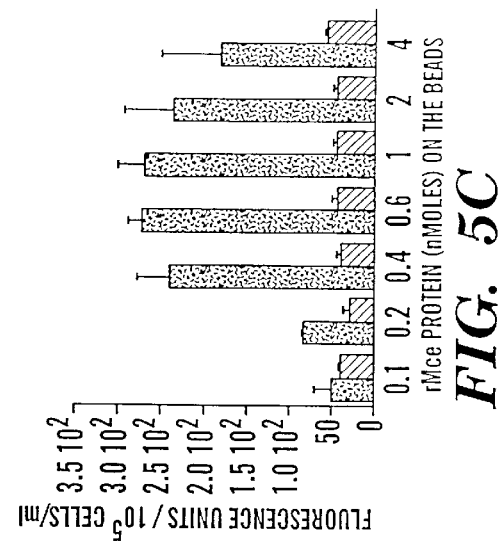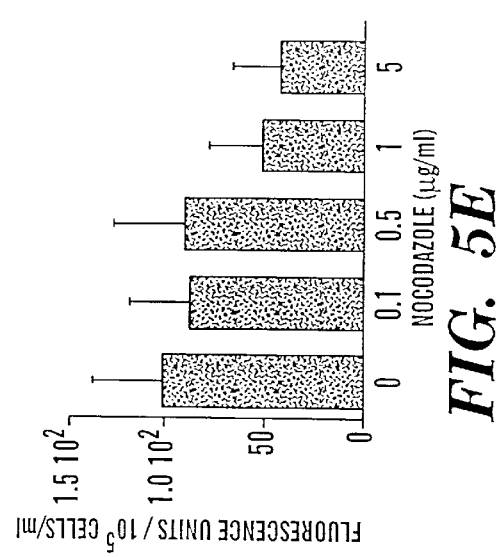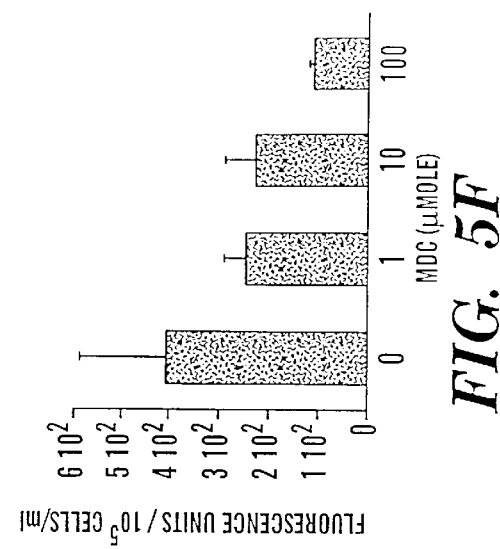

(12) United States Patent US 6,399,764 B1

DNA MOLECULE ENCODING FOR CELLULAR UPTAKE OF *MYCOBACTERIUM TUBERCULOSIS* AND USES THEREOF

This application is a divisional of U.S. patent application Ser. No. 08/907,229, filed Aug. 6, 1997, now U.S. Pat. No. 6,072,048, which claims the benefit of U.S. Provisional Patent Application Serial No. 60/040,097, filed Mar. 10, 1997, which are hereby incorporated by reference.

This invention was developed with government funding under National Institutes of Health Grant No. RO1 AI35266. The U.S. Government may retain certain rights.

FIELD OF THE INVENTION

The present invention relates to a DNA molecule encoding for uptake of *Mycobacterium tuberculosis* and its use in drugs, vaccines, and diagnostic tests.

BACKGROUND OF THE INVENTION

Tuberculosis is the leading cause of death in the world with an estimated 9 million new cases of tuberculosis and 2.9 million deaths occurring from the disease each year. In the United States, the steadily declining incidents of tuberculosis has been reversed since 1985. This problem is compounded by the increasing incidence of drug-resistant strains of *Mycobacterium tuberculosis*.

Recent outbreaks of tuberculosis have involved settings in which a large number of HIV-infected persons resided in close proximity (e.g., AIDS wards in hospitals, correctional facilities, and hospices) Transmission of tuberculosis to health care workers occurred in these outbreaks; 18 to 50% of such workers showed a conversion in their skin tests. See F. Laraque et. al., "Tuberculosis in HIV-Infected Patients," *The AIDS Reader* (September/October 1992), which is hereby incorporated by reference.

There are two basic clinical patterns that follow infection with *Mycobacterium tuberculosis*.

In the majority of cases, inhaled tubercle bacilli ingested by phagocytic alveolar macrophages are either directly killed or grow intracellularly to a limited extent in local lesions called tubercles. Infrequently in children and immunocompromised individuals, there is early hematogenous dissemination with the formation of small miliary (millet-like) lesions or life-threatening meningitis. More commonly, within 2 to 6 weeks after infection, cell-mediated immunity develops, and infiltration into the lesion of immune lymphocytes and activated macrophages results in the killing of most bacilli and the walling-off of this primary infection, often without symptoms being noted by the infected individual. Skin-test reactivity to a purified protein derivative ("PPD") of tuberculin and, in some cases, X-ray evidence of a healed, calcified lesion provide the only evidence of the infection. Nevertheless, to an unknown extent, dormant but viable *Mycobacterium tuberculosis* bacilli persist.

The second pattern is the progression or breakdown of infection to active disease. Individuals infected with *Mycobacterium tuberculosis* have a 10% lifetime risk of developing the disease. In either case, the bacilli spread from the site of initial infection in the lung through the lymphatics or blood to other parts of the body, the apex of the lung and the regional lymph node being favored sites. Extrapulmonary tuberculosis of the pleura, lymphatics, bone, genito-urinary system, meninges, peritoneum, or skin occurs in about 15% of tuberculosis patients. Although many bacilli are killed, a large proportion of infiltrating phagocytes and lung parenchymal cells die as well, producing characteristic solid caseous (cheese-like) necrosis in which bacilli may survive but not flourish. If a protective immune response dominates, the lesion may be arrested, albeit with some residual damage to the lung or other tissue. If the necrotic reaction expands, breaking into a bronchus, a cavity is produced in the lung, allowing large numbers of bacilli to spread with coughing to the outside. In the worst case, the solid necrosis, perhaps a result of released hydrolases from inflammatory cells, may liquefy, which creates a rich medium for the proliferation of bacilli, perhaps reaching $10^9$ per milliliter. The pathologic and inflammatory processes produce the characteristic weakness, fever, chest pain, cough, and, when a blood vessel is eroded, bloody sputum.

Ignorance of the molecular basis of virulence and pathogenesis is great. It has been suggested that the establishment of molecular evidence regarding avirulent strains, the identification and cloning of putative virulence genes of the pathogen, and the demonstration that virulence can be conveyed to an avirulent strain by those genes is necessary. Although avirulent strains of *Mycobacterium tuberculosis* exist, the nature of the mutations is unknown. Not a single gene involved in the pathogenesis of tuberculosis has been defined in the prior art. The molecular bases of invasion of host cells, intracellular survival, growth, spread, or tissue tropism also have not been known. None of the targets of existing drugs has been characterized at a molecular level, and the mechanism of resistance to any drug has not been defined; no new mycobacterial target for drug development has been characterized in 20 years.

There have been many prescribed treatment regimens for tuberculosis. The regimen recommended by the U.S. Public Health Service and the American Thoracic Society is a combination of isoniazid, rifampicin, and pyrazinamide for two months followed by administration of isoniazid and rifampicin for an additional four months. In persons with HIV infection, isoniazid and rifampicin treatment are continued for an additional seven months. This treatment, called the short-course chemotherapy, produces a cure rate of over 90% for patients who complete it. Treatment for multi-drug resistant tuberculosis requires addition of ethambutol and/or streptomycin in the initial regimen, or second line drugs, such as kanamycin, amikacin, capreomycin, ethionamide, cyclcoserine, PAS, and clofazimin. New drugs, such as ciprofloxacin and ofloxacin can also be used. For individuals infected with conventional *Mycobacterium tuberculosis* and showing PPD positive results, chemoprophylaxis with isoniazid has been about 90% effective in preventing the disease. Tuberculosis and these treatments are discussed in more detail in B. Bloom et. al., "Tuberculosis: Commentary on a Reemergent Killer," *Science*, 257:1055–64 (1992); "Control of Tuberculosis in the United States," *American Thoracic Society*, 146:1623–33 (1992); and *City Health Information*, vol. 11 (1992), which is hereby incorporated by reference.

Although the currently used treatments for tuberculosis have a relatively high level of success, the need remains to improve the success rate for treating this disease. Moreover, in view of the ever-increasing level of *Mycobacterium tuberculosis* strains which are resistant to conventional treatment regimens, new types of treatment must be developed. In high tuberculosis endemic areas, both in the United States and abroad, such resistant strains are becoming increasingly present.

SUMMARY OF THE INVENTION

The present invention relates to isolated DNA molecules which confers on *Mycobacterium tuberculosis* an ability to enter mammalian cells as well as isolated proteins or polypeptides encoded by those isolated DNA molecules. The molecules can be inserted as heterologous DNA in an expression vector forming a recombinant DNA expression system for producing the proteins or peptides. Likewise, the heterologous DNA, usually inserted in an expression vector to form a recombinant DNA expression system can be incorporated in a cell to achieve this objective.

The isolated proteins or polypeptides of the present invention can be combined with a pharmaceutically-acceptable carrier to form a vaccine or used alone for administration to mammals, particularly humans, for preventing infection by *Mycobacterium tuberculosis*. The proteins or polypeptides of the present invention can be used to raise an antibody or a binding portion thereof. The antibody or binding portion thereof may be used alone or combined with a pharmaceutically-acceptable carrier to treat mammals, particularly humans, already exposed to *Mycobacterium tuberculosis* to induce a passive immunity to prevent disease occurrence.

The proteins or polypeptides of the present invention or the antibodies or binding portions thereof raised against them can also be utilized in a method for detection of *Mycobacterium tuberculosis* in a sample of tissue or body fluids. When the proteins or polypeptides are utilized, they are provided as an antigen. Any reaction with the antigen or the antibody is detected using an assay system which indicates the presence of *Mycobacterium tuberculosis* in the sample. Alternatively, *Mycobacterium tuberculosis* can be detected in such a sample by providing a nucleotide sequence of the gene conferring on *Mycobacterium tuberculosis* an ability to enter mammalian cells as a probe in a nucleic acid hybridization assay or a gene amplification detection procedure (e.g., using a polymerase chain reaction procedure). Any reaction with the probe is detected so that the presence of *Mycobacterium tuberculosis* in the sample is indicated.

The proteins or polypeptides of the present invention can also be used for purposes unrelated to the treatment or detection of *Mycobacterium tuberculosis*. More particularly, the ability of those proteins or polypeptides to confer on *Mycobacterium tuberculosis* an ability to enter mammalian cells can be utilized to permit such cells to uptake other materials. This can be achieved with a product that includes a material for uptake by mammalian cells and the proteins or polypeptides of the present invention associated with that material.

Isolation of the DNA molecules of the present invention constitutes a significant advance in the treatment and detection of such bacteria. It also provides the basis for a vaccine to prevent infection by *Mycobacterium tuberculosis* and a pharmaceutical agent for passive immunization for those exposed to *Mycobacterium tuberculosis*. The proteins utilized in the vaccine or to produce the pharmaceutical agent can be produced at high levels using recombinant DNA technology.

In diagnostic applications, the proteins or polypeptides of the present invention as well as antibodies and binding portions thereof against them permit rapid determination of whether a particular individual is infected with *Mycobacterium tuberculosis*. Moreover, such detection can be carried out without requiring an examination of the individual being tested for an antibody response.

Aside from the development of treatments and diagnostic tools for *Mycobacterium tuberculosis*, the present invention's ability to confer entry of such organisms into mammalian cells has significant utility in therapeutic treatments requiring the introduction of materials into cells, particularly to macrophages. By associating the protein or polypeptide of the present invention with pharmaceutical agents, such agents can be rapidly introduced into cells for treatment thereof. The enhanced cellular uptake of such products can reduce drug dosages, thus reducing toxicity and cost. For example, in conventional cancer treatment, drug toxicity is a major problem due to the requirement for administration of large dosages; the present invention has the potential to reduce such high dosage levels while enabling delivery of equivalent or higher drug levels intracellularly.

Furthermore, binding the proteins or polypeptides of the present invention to DNA fragments can be utilized in conjunction with gene therapy regimens. In particular, the ability of the encoded product of the DNA molecules of the present invention to augment uptake into macrophages provides an opportunity to deliver genes specifically to macrophages. Such a system can be used to induce not only humoral immunity but cell-mediated immunity.

BRIEF DESCRIPTION OF THE DRAWINGS

FIG. 5 shows fluorescence emission determinations of fluorescent latex microspheres associating with HeLa cells. In FIG. 5(A), rMcep1-coated beads were incubated with HeLa cells (black bars) and compared to the same beads coated with *E. coli* BL21 (DE3) protein lysate (gray bars) prepared as described. Maximum uptake of the beads was achieved as early as 12 hrs. In FIG. 5(B), beads coated with 2.5 mg/ml of rMcep1 were incubated with the HeLa cells preincubated with the indicated concentrations of solubilized rMcep1. Increasing concentrations of the unbound protein competitively blocked the uptake of the beads. In FIG. 5 (C), the beads were coated with the indicated concentrations of rMcep1 (black bars) or rMcep2 (gray bars), an rMcep1 truncated (58 amino acid residues) at the N-terminus. No increase in uptake was observed at rMcep1 concentrations >0.6 nmoles. A decrease in uptake at higher concentrations indicated competitive inhibition by the unbound protein fraction. Equimolar concentrations of rMcep2 promoted no uptake of the beads. In FIGS. 5(D–F), cytochalasin D, an inhibitor of microfilament assembly, blocked uptake of the fluorescent beads, but the inhibition was not complete at a maximum concentration that was not cytotoxic to HeLa cells. Nocodazole, an inhibitor of microtubule assembly, had a similar inhibitory effect at noncytotoxic concentrations. A combination of cytochalasin D and nocodazole at 0.1 mg/ml each was cytotoxic. Monodansylcadaverine (MDC), an inhibitor of coated vesicle formation, also partly inhibited the bead uptake.

FIG. 6 is a transmission electron microscopy of 0.3 mm latex beads incubated with HeLa cells for 4 hrs. Finger-like projections of the HeLa cell membrane around the rMcep1-coated beads indicates phagocytosis involving microfilament rearrangement (FIG. 6 (A)), while the membrane invagination and formation of bristle-like structures (most likely coathrin coats) at the penetrating head of the bead (see arrows) indicates receptor-mediated endocytosis (see FIG. 6 (B)). Bars=0.1 mm.

DETAILED DESCRIPTION OF THE INVENTION

The present invention relates to an isolate DNA molecules conferring on *Mycobacterium tuberculosis* an ability to enter mammalian cells. This DNA molecule comprises the nucleotide sequence corresponding to SEQ. ID. No. 1 as follows:

```
atgtcttttg gtccttcttg gaggccctca tcatcactgc gatcgtcatg gtcagccact    60
gctactacgg gtacgccgcc ggtggaggcc ccgtcggtgt cggcgaggcc gtcggccgat   120
cgatgcgttt ctcgttggtc tcggtgcagg tcgttgtcct gtttgcagcg ttggcgctct   180
acggtgtcga cccgaacttc aatctcacgg tgtagccgca tgacgacgcc ggggaagctg   240
aacaaggcgc gagtgccgcc ctacaagacg gcgggtttgg gtctagtgct ggtcttcgcg   300
ctcgtagttg ccttggtata cctgcagttt cgcggggagt tcacgcccaa gacgcagttg   360
acgatgctgt ccgctcgtgc gggtttggtq atggatcccg ggtcgaaggt cacctataac   420
ggggtggaga tcgggcgggt agacaccatc tcggaggtca cacgtgacgg cgagtcggcg   480
gccaagttca tcttggatgt ggatccgcgt tacatccacc tgattccggc aaatgtgaac   540
gccgacatca aggcgaccac ggtgttcggc ggtaagtatg tgtcgttgac cacgccgaaa   600
aacccgacaa agaggcggat aacgccaaaa gacgtcatcg acgtacggtc ggtgaccacc   660
gagatcaaca cgttgttcca gacgctcacc tcgatcgccg agaaggtgga tccggtcaag   720
ctgaacctga ccctgagcgc ggccgcggag gcgttgaccg ggctgggcga taagttcggc   780
gagtcgatcg tcaacgccaa caccgttctg gatgacctca attcgcggat gccgcaqtcg   840
cgccacgaca ttcagcaatt ggcggctctg ggcgacgtct acgccgacgc ggcgccggac   900
ctgttcgact ttctcgacag ttcggtgacc accgcccgca ccatcaatgc ccagcaagcg   960
gaactggatt cggcgctgtt ggcggcggcc gggttcggca acaccacagc cgatgtcttc  1020
gaccgcggcg ggccgtatct gcagcggggg gtcgccgacc tggtccccac cgccaccctg  1080
ctcgacactt atagcccgga actgttctgc acgatccgca acttctacga tgccgatccg  1140
ctcgctaaag cggcgtccgg tggcggtaac ggctactcgc tgaggacgaa ctcagagatc  1200
ctatccggga taggtatctc cttgttgtct cccctggcgt tagccaccaa tggggcggca  1260
atcggaatcg gactggtagc cggattgata gcgccgcccc tcgcggtggc cgcaaatcta  1320
gcgggagccc tacccggaat cgttggcggc gcgcccaatc cctataccta tccggagaat  1380
ctgccgcggg tgaacgctcg cggtggcccg gggggcgccc ccggttgctg gcagccgatc  1440
```

Figure 1A:
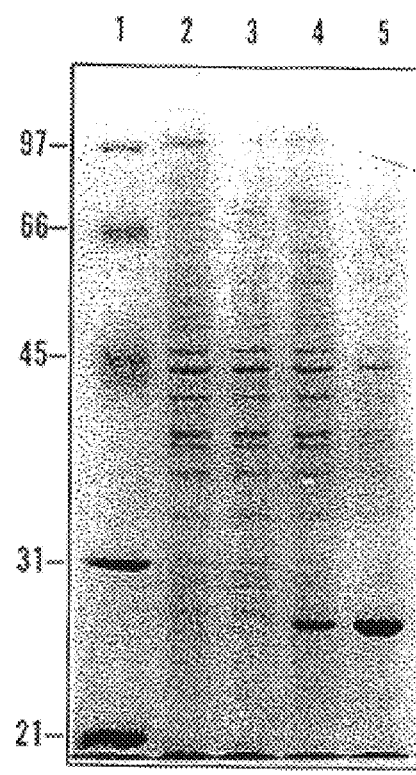
FIG. 1(A) is an SDS polyacrylamide gel electrophoresis analysis of the product of recombinant plasmid pETmcel. Whole bacterial cell lysates of *E. coli* BL21 (lane 2), BL21 (pET23c) (lane 3), BL21 (pETmcel), uninduced (lane 4), and BL21 (pETmcel), induced for 2 hrs with IPTG (lane 5) were resolved in a 12.5% SDS polyacrylamide gel and stained with Coomassie Blue (A). A protein of about 27 kDa (arrow) is expressed by *E. coli* BL21 carrying pETmcel.

```
                                             -continued
acccgggatc tgtggccagc gccgtatctg gtgatggaca ccggtgccag cctcgccccg   1500
tacaaccaca tggaggttgg ctcgcctat gcagtcgagt acgtctgggg ccgtcaggta   1560
ggggataaca cgatcaaccc atga                                         1584
```

In addition to the DNA molecule having the nucleic acid sequence of SEQ. ID. No. 1, the present invention encompasses portions of this molecule, including the DNA molecules with a nucleic acid sequence comprising base 1 to base 501 of SEQ. ID. No. 1, a nucleic acid sequence comprising base 285 to base 501 of SEQ. ID. No. 1, a nucleic acid sequence comprising base 285 to base 1584 of SEQ. ID. No. 1, or a nucleic acid sequence comprising base 1137 to base 1584 of SEQ. ID. No. 1. The DNA molecule with a nucleic acid sequence comprising base 285 to base 1584 of SEQ. ID. No. 1 has a molecular weight of about 45 kDa. The amino acid sequences, deduced from the nucleotide sequences, represent highly hydrophilic proteins with a hydrophobic region at their carboxy terminus. They could be secreted proteins, cytoplasmic proteins, or surface proteins with the carboxy terminus attached to the outer membrane of the organism. It is believed that the protein or polypeptide encoded by the DNA molecule having a nucleic acid sequence of SEQ. ID. No. 1 has the deduced amino acid sequence corresponding to SEQ. ID. No. 2 as follows:

```
Met Ser Phe Gly Pro Ser Trp Arg Pro Ser Ser Ser Leu Arg Ser Ser
 1               5                  10                  15

Trp Ser Ala Thr Ala Thr Thr Gly Thr Pro Pro Val Glu Ala Pro Ser
                20                  25                  30

Val Ser Ala Arg Pro Ser Ala Asp Arg Cys Val Ser Arg Trp Ser Arg
                35                  40                  45

Cys Arg Ser Leu Ser Cys Leu Gln Arg Trp Arg Ser Thr Val Ser Thr
         50                  55                  60

Arg Thr Ser Ile Ser Arg Cys Ser Arg Met Thr Thr Pro Gly Lys Leu
 65                  70                  75                  80

Asn Lys Ala Arg Val Pro Pro Tyr Lys Thr Ala Gly Leu Gly Leu Val
                85                  90                  95

Leu Val Phe Ala Leu Val Val Ala Leu Val Tyr Leu Gln Phe Arg Gly
               100                 105                 110

Glu Phe Thr Pro Lys Thr Gln Leu Thr Met Leu Ser Ala Arg Ala Gly
              115                  120                 125

Leu Val Met Asp Pro Gly Ser Lys Val Thr Tyr Asn Gly Val Glu Ile
    130                  135                 140

Gly Arg Val Asp Thr Ile Ser Glu Val Thr Arg Asp Gly Glu Ser Ala
145                  150                 155                 160

Ala Lys Phe Ile Leu Asp Val Asp Pro Arg Tyr Ile His Leu Ile Pro
                 165                 170                 175

Ala Asn Val Asn Ala Asp Ile Lys Ala Thr Thr Val Phe Gly Gly Lys
                180                  185                 190

Tyr Val Ser Leu Thr Thr Pro Lys Asn Pro Thr Lys Arg Arg Ile Thr
         195                 200                 205

Pro Lys Asp Val Ile Asp Val Arg Ser Val Thr Glu Ile Asn Thr
    210                  215                 220

Leu Phe Gln Thr Leu Thr Ser Ile Ala Glu Lys Val Asp Pro Val Lys
225                  230                  235                 240

Leu Asn Leu Thr Leu Ser Ala Ala Ala Glu Ala Leu Thr Gly Leu Gly
                 245                 250                 255

Asp Lys Phe Gly Glu Ser Ile Val Asn Ala Asn Thr Val Leu Asp Asp
                 260                 265                 270

Leu Asn Ser Arg Met Pro Gln Ser Arg His Asp Ile Gln Gln Leu Ala
    275                  280                 285

Ala Leu Gly Asp Val Tyr Ala Asp Ala Ala Pro Asp Leu Phe Asp Phe
                 290                 295                 300
```

```
                        -continued
Leu Asp Ser Ser Val Thr Thr Ala Arg Thr Ile Asn Ala Gln Gln Ala
305                 310                 315                 320

Glu Leu Asp Ser Ala Leu Leu Ala Ala Ala Gly Phe Gly Asn Thr Thr
                325                 330                 335

Ala Asp Val Phe Asp Arg Gly Gly Pro Tyr Leu Gln Arg Gly Val Ala
            340                 345                 350

Asp Leu Val Pro Thr Ala Thr Leu Leu Asp Thr Tyr Ser Pro Glu Leu
        355                 360                 365

Phe Cys Thr Ile Arg Asn Phe Tyr Asp Ala Asp Pro Leu Ala Lys Ala
    370                 375                 380

Ala Ser Gly Gly Gly Asn Gly Tyr Ser Leu Arg Thr Asn Ser Glu Ile
385                 390                 395                 400

Leu Ser Gly Ile Gly Ile Ser Leu Leu Ser Pro Leu Ala Leu Ala Thr
                405                 410                 415

Asn Gly Ala Ala Ile Gly Ile Gly Leu Val Ala Gly Leu Ile Ala Pro
            420                 425                 430

Pro Leu Ala Val Ala Ala Asn Leu Ala Gly Ala Leu Pro Gly Ile Val
        435                 440                 445

Gly Gly Ala Pro Asn Pro Tyr Thr Tyr Pro Glu Asn Leu Pro Arg Val
    450                 455                 460

Asn Ala Arg Gly Gly Pro Gly Gly Ala Pro Gly Cys Trp Gln Pro Ile
465                 470                 475                 480

Thr Arg Asp Leu Trp Pro Ala Pro Tyr Leu Val Met Asp Thr Gly Ala
                485                 490                 495

Ser Leu Ala Pro Tyr Asn His Met Glu Val Gly Ser Pro Tyr Ala Val
            500                 505                 510

Glu Tyr Val Trp Gly Arg Gln Val Gly Asp Asn Thr Ile Asn Pro Xaa
        515                 520                 525
``` where Xaa is a stop codon.

In addition to the protein or polypeptide having the amino acid sequence of SEQ. ID. No. 2, the present invention encompasses portions thereof, including the proteins or polypeptides with an amino acid sequence comprising amino acid 1 to amino acid 167 of SEQ. ID. No. 2, an amino acid sequence comprising amino acid 95 to amino acid 167 of SEQ. ID. No. 2, an amino acid sequence comprising amino acid 95 to amino acid 528 of SEQ. ID. No. 2, or an amino acid sequence comprising amino acid 379 to amino acid 528 of SEQ. ID. No. 2. The protein or polypeptide with an amino acid sequence comprising amino acid 95 to amino acid 528 of SEQ. ID. No. 2 has a molecular weight of about 45 kDa.

Production of this isolated protein or polypeptide is preferably carried out using recombinant DNA technology. The protein or polypeptide is believed to have one or more antigenic determinants conferring on *Mycobacterium tuberculosis* an ability to enter mammalian cells.

The proteins or polypeptides of the present invention are preferably produced in purified form by conventional techniques. To isolate the proteins, the *E. coli* host cell carrying a recombinant plasmid is propagated, homogenized, and the homogenate is centrifuged to remove bacterial debris. The supernatant is then subjected to sequential ammonium sulfate precipitation. The fraction containing the proteins of the present invention are subjected to gel filtration in an appropriately sized dextran or polyacrylamide column to separate the proteins. If necessary, the protein fraction may be further purified by HPLC.

Any one of the DNA molecules conferring on *Mycobacterium tuberculosis* an ability to enter mammalian cells can be incorporated in cells using conventional recombinant DNA technology. Generally, this involves inserting the selected DNA molecule into an expression system to which that DNA molecule is heterologous (i.e. not normally present). The heterologous DNA molecule is inserted into the expression system or vector in proper orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promotors. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Additionally, any SD-ATG combination produced by recombinant DNA or other techniques involving incorporation of synthetic nucleotides may be used.

Once the desired isolated DNA molecule conferring on *Mycobacterium tuberculosis* an ability to enter mammalian cells has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

Generally, the human immune system responds to infection by pathogenic bacteria by producing antibodies that bind to specific proteins or carbohydrates on the bacterial surface. The antibodies stimulate binding to macrophages which have receptors that bind to the $F_c$ region of the antibodies. Other serum proteins, called complement, coat the foreign particle and stimulate their ingestion by binding to specific surface receptors on the macrophage. Once the particle is bound to the surface of the macrophage, the sequential process of ingestion begins by continual apposition of a segment of the plasma membrane to the particle surface. Surface receptors on the membranes then interact with ligands distributed uniformly over the particle surface to link the surfaces together. The macrophage enveloping the particle is then delivered to lysosomes where the particle is ingested.

Some organisms are ingested (i.e. undergo uptake) by macrophages but are not killed. Amongst these is *Mycobacterium tuberculosis*. As a result, such organisms are able to survive indefinitely within macrophages and, when they escape from the macrophage, cause active tuberculosis.

In view of the present invention’s determination of nucleotide sequences conferring on *Mycobacterium tuberculosis* an ability to enter mammalian cells, the molecular basis for *Mycobacterium tuberculosis* uptake is suggested. With this information and the above-described recombinant DNA technology, a wide array of therapeutic and/or prophylatic agents and diagnostic procedures for, respectively, treating and detecting *Mycobacterium tuberculosis* can be developed.

For example, an effective amount of the proteins or polypeptides of the present invention can be administered alone or in combination with a pharmaceutically-acceptable carrier to humans, as a vaccine, for preventing infection by *Mycobacterium tuberculosis*. Alternatively, it is possible to administer to individuals exposed to *Mycobacterium tuberculosis* an effective amount of an antibody or binding portion thereof against these proteins or polypeptides as a passive immunization. Such antibodies or binding portions thereof are administered alone or in combination with a pharmaceutically-acceptable carrier to effect short term treatment of individuals who may have been recently exposed to *Mycobacterium tuberculosis*.

Antibodies suitable for use in inducing passive immunity can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest (i.e. the protein or peptide of the present invention) either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with one of the proteins or polypeptides of the present invention. Such immunizations are repeated as necessary at intervals of up to several weeks to obtain a sufficient titer of antibodies. The virus is carried in appropriate solutions or adjuvants. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol (PEG) or other fusing agents (See Milstein and Kohler, *Eur. J. Immunol.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering one of the proteins or polypeptides of the present invention subcutaneously to New Zealand white rabbits which have first been bled to obtain pre-immune serum. The antigens can be injected at a total volume of 100 $\mu$l per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbitol 150 mg/Kg IV. This and other procedures for raising polyclonal antibodies are disclosed in E. Harlow, et. al., editors, *Antibodies: A Laboratory Manual* (1988), which is hereby incorporated by reference. For instance, see Example 9 infra.

In addition to utilizing whole antibodies, the process of the present invention encompasses use of binding portions of such antibodies. Such antibody fragments can be made by conventional procedures, such as proteolytic fragmentation procedures, as described in J. Goding, *Monoclonal Antibodies: Principles and Practice*, pp. 98–118 (N.Y. Academic press 1983), which is hereby incorporated by reference.

The vaccines and passive immunization agents of this invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the proteins or peptides of the present invention or the antibodies or binding portions thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The proteins or polypeptides of the present invention or the antibodies or binding portions thereof of this invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the proteins or polypeptides of the present invention or the antibodies or binding portions thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In yet another aspect of the present invention, the proteins or polypeptides of the present invention can be used as antigens in diagnostic assays for the detection of *Mycobacterium tuberculosis* body fluids. Alternatively, the detection of that bacillus can be achieved with a diagnostic assay employing antibodies or binding portions thereof raised by such antigens. Such techniques permit detection of *Mycobacterium tuberculosis* in a sample of the following tissue or body fluids: blood, spinal fluid, sputum, pleural fluids, urine, bronchial alveolor lavage, lymph nodes, bone marrow, or other biopsied materials.

In one embodiment, the assay system has a sandwich or competitive format. Examples of suitable assays include an enzyme-linked immunosorbent assay, a radioimmunoassay, a gel diffusion precipitan reaction assay, an immunodiffusion assay, an agglutination assay, a fluorescent immunoassay, a protein A immunoassay, or an immunoelectrophoresis assay.

In an alternative diagnostic embodiment of the present invention, the nucleotide sequences of the isolated DNA molecules of the present invention may be used as a probe in nucleic acid hybridization assays for the detection of *Mycobacterium tuberculosis* in various patient body fluids. The nucleotide sequences of the present invention may be used in any nucleic acid hybridization assay system known in the art, including, but not limited to, Southern blots (Southern, *J. Mol. Biol.*, 98:508 (1975)); Northern blots (Thomas et al., *Proc. Nat'l Acad. Sci. USA*, 77:5201–05 (1980)); Colony blots (Grunstein et al., *Proc. Nat'l Acad. Sci. USA*, 72:3961–65 (1975), which are hereby incorporated by reference). Alternatively, the isolated DNA molecules of the present invention can be used in a gene amplification detection procedure (e.g., a polymerase chain reaction). See H. A. Erlich et. al., "Recent Advances in the Polymerase Chain Reaction", *Science* 252:1643–51 (1991), which is hereby incorporated by reference.

More generally, the molecular basis for the uptake phenomenon achieved by *Mycobacterium tuberculosis* can be utilized to effect uptake of other materials into mammalian cells. This is achieved by utilizing the proteins or polypeptides of the present invention which effect cellular uptake in association with such materials for uptake by mammalian cells. This phenomenon can be used to introduce a wide variety of materials into such cells, including antibiotics, DNA fragments, anti-neoplastic agents, and mixtures thereof.

The opportunity for direct cell entry of antibiotics constitutes a substantial advance, because they will be able to kill intracellular Mycobacterium tuberculosis. One approach for achieving such uptake is by impregnating microspheres with antibiotics and then coating the spheres with the cellular uptake proteins or polypeptides of the present invention in order to achieve such uptake. Alternatively, instead of utilizing microspheres to transport antibiotics, such therapeutics can be chemically linked to the cellular uptake proteins or polypeptides of the present invention.

This technology can be used to treat a wide array of diseases caused by intracellular pathogens. For treatment of tuberculosis, a repertoire of antibiotics, having themselves poor cellular penetration but high activity against extracellular *Mycobacterium tuberculosis* when tested in vitro, can be utilized in conjunction with the cellular uptake proteins or polypeptides of the present invention. In cancer treatment, intracellular delivery of anti-neoplastic agents can be greatly enhanced by conjugating such agents to the cellular uptake proteins or polypeptides of the present invention. This will enable reductions in dosages for such agents and in their resulting toxicity.

Another aspect of the present invention is to utilize the cellular uptake proteins or polypeptides of the present invention in gene therapy or in a genetic vaccine where pieces of therapeutically or prophylactically useful DNA are conjugated at their thymine residues to the proteins or polypeptides of the present invention via linker arms. As a result, genetic material can be introduced into cells to correct genetic defects or to produce a desired characteristic or products that serve as immunogens.

EXAMPLES

Example 1

Bacterial Strains and Plasmids.

The genomic DNA used in the study was derived from *M. tuberculosis* H37Ra (ATCC 25177). The vector used in the construction of the partial SauIIIA1 genomic library was pBluescript II SK-(pBS, Stratagene, La Jolla, Calif.). The recombinant plasmid pZX7 is a pbluescript containing a 1535-bp *M. tuberculosis* DNA fragment associated with mammalian cell entry (EMBL accession number X70901) (Arruda et al., "Cloning of an *M. tuberculosis* DNA Fragment Associated With Entry and Survival Inside Cells," *Science* 261:1454–57 (1993), which is hereby incorporated by reference). The pET23 (Novagen, Madison, Wis.) and pQE series (Qiagen Inc, Chatsworth, Calif.) of plasmids were used as expression vectors. *E. coli* BL21(DE3) and M15(pREP4) were used as hosts for these vectors, respectively, as recommended by the manufacturers. A recombinant plasmid pQENO14, containing an unrelated 680-bp *M. tuberculosis* DNA fragment that expresses a 24 kDa recombinant protein was used as a negative control.

Example 2

Genetic Techniques.

A 627-bp putative open reading frame (referred to as mycobacterium cell entry sequence or mce1) found in the 1535-bp DNA insert of pZX7 was subcloned into pET23 vectors in 3 different reading frames after it was amplified by PCR with primers that introduced EcoRI and HinDIII restriction sites at its ends. The resulting recombinant plasmid pET23mce1 was used to subclone its BamHI-HinDIII fragment into pQE32, which allowed the plasmid to express the same mce1 product with a polyhistidine (6xHis) tag at its N-terminus (pQEmce1). The pET23 vector is designed to express a fusion protein with a 12-amino acid T7 tag at the N-terminus. These two expression systems were used to exclude the possibility that the carrier plasmid-encoded sequences contributed to the cell uptake activity. An mce1 fragment with a 174-bp segment deleted at the 5' end (mce2), which expressed a truncated mce1 product, was also subcloned into pQE32 as a control Because of the possibility (as noted below) that the sequence downstream of the 627-bp sequence in the originally cloned 1535-bp DNA fragment does not occur in that position in the native *M. tuberculosis* chromosome, a large (4.8 kb) SauIIIA fragment of *M. tuberculosis* containing the 627-bp fragment was sequenced to ascertain the sequences surrounding the mce1 locus.

Example 3

Protein Expression and Purification.

*E. coli* BL21(DE3) that harbored pET23mce1 and *E. coli* M15(pREP4) containing pQEmce1 were grown overnight in 5 ml TSB containing ampicillin (200 mg/ml) and a 500-ml aliquot of the bacterial suspension was pelleted, resuspended in 5 ml of fresh tryptic soy broth, and incubated for 3 hrs at 37° C. Then 50 ml of IPTG (40 mM) were added to the growth and incubated for 2 hrs at 37° C. The induced and uninduced recombinant *E. coli* strains, and control *E. coli* strains (BL21[DE3] and M15[pREP4]) were analyzed by SDS-polyacrylamide gel electrophoresis.

The newly expressed protein formed an inclusion body in the recombinant *E. coli* strains. The inclusion body was therefore purified according to instructions of the expression vectors' respective manufacturers (Qiagen Inc). The polyhistidine-tagged protein was separated on a Ni-NTA resin column. The protein was separated by SDS-PAGE and analyzed for purity by silver staining according to the method of Morissey (Morissey, J. H., "Silver Strain for Proteins in Polyacrylamide Gels: A Modified Procedure With Enhanced Uniform Sensitivity," *Anal. Biochem.* 117:307–10 (1981), which is hereby incorporated by reference).

Example 4

Immunoelectron Microscopy and Inmunoblot Analysis.

A polyclonal antibody raised in female NZW rabbits against the mce1 product expressed in *E. coli* BL21 (pET23mce1) was used in the following experiments. A bacterial pellet (containing approximately $10^7$ organisms) from a 5-day growth and a 3-week growth in 7H9 medium of *M. tuberculosis* H37Ra strain was fixed in 3% glutaraldehyde in PBS (pH 7.6) for 24 hrs and exposed at RT for 30 min to 1:1000 dilution of the rabbit antibody raised against the mce1 product or pre-vaccination serum. The suspension was then incubated at RT for 30 min with colloidal gold suspension containing 5-nm gold particles ($1.9 \times 10^{13}$ particles/ml) conjugated to anti-rabbit IgG goat antibody. The cells were stained with 0.1% uranyl acetate in water and examined with JEOL Model 100CX-II electron microscope (JEOL, Inc., Japan).

*M. tuberculosis* H37Ra subcellular fractions (cell wall, membrane, and cytosol) made available through the program on "Tuberculosis Research Materials" of the National Institute of Allergy and Infectious Diseases, were kindly provided by John Belisle (Colorado State University, Fort Collins). Approximately 5 mg of each fraction were resolved by SDS-PAGE, transferred onto a piece of nitrocellulose membrane, and immunoblotted with the antibody raised against the mce1 product (recombinant Mce1 protein, or rMcep1).

Example 5

Latex Microsphere Uptake.

A 4-ml sample of the stock suspensions of latex beads (containing about $3 \times 10^{10}$/ml of 0.3 mm-diameter beads or $5 \times 10^8$/ml of 1.1 mm-diameter beads) (Sigma, St. Louis) was mixed in 1 ml of PBS containing 50 mg/ml of the rMcep1, and incubated for 2 hrs at 37° C. A 100-ml sample of this suspension was then added to a near-confluent HeLa cell monolayer grown over a glass cover slip in a well containing 2 ml of MEM in a 24-well polystyrene tissue culture plate. The cells were incubated at 37° C. for 5 hrs in a $CO_2$ incubator, washed 5 times with PBS, fixed with 100% methanol, and stained with 10% Giemsa stain.

The cells were also prepared for examination by transmission electron microscopy. After the indicated incubation periods, the glutaraldehyde-fived (2% in PBS, pH 7.6) cells were post-fixed in 1% osmium tetroxide in PBS, dehydrated through graded ethanol solutions, and embedded in Spurr's low viscosity embedding media. The ultra thin sections were stained with uranyl acetate and lead citrate, and examined by JEOL Model 100CX-II electron microscope.

Fluorescence emission by the protein-coated 1.0 mm fluorescent latex beads (Sigma) was measured to quantitate the levels of bead association with HeLa cells. The fluorescent beads (stock suspension containing approximately $5 \times 10^8$ beads/ml) were coated as above and fluorescence emission (in fluorescence units/$10^5$ cells) per well was detected directly from a 24-well plate by Cytofluor reader (Millipore, Bedford, Mass.).

As controls, one set of the fluorescent beads was coated with the lysate of *E. coli* BL21 (DE3) or M15(pREP4) hosts carrying pET23c or pQE32 processed by the same protein purification scheme described above. Uncoated beads and beads coated with BSA, an N-terminus truncated derivative of Mcel (expressed by pQE32mce2), and an unrelated recombinant *M. tuberculosis* protein (expressed from pQEN014) were also used as controls.

Example 6

Inhibition of Latex Microsphere Uptake.

Cytochalasin D specifically inhibits phagocytosis by disrupting microfilament assembly, and nocodazole inhibits the endocytic pathway by blocking microtubule assembly (Carter, S. B., "Effects of Cytochalasins on Mammalian Cells," *Nature* 213:261–4 (1967) and Parczyk et al., "Microtubules Are Involved in the Secretion of Proteins at the Apical Cell Surface of the Polarized Epithelial Cells, Madin-Darby Canine Kidney," *J. Biol. Chem.* 264:16837–46 (1989), which are hereby incorporated by reference). Monodansylcadaverine (MDC) inhibits formation and internalization of clathrin-coated vesicles (Schlegel et al., "Amantadine and Dansylcadaverine Inhibit Vesicular Stomatitis Virus Uptake and Receptor-mediated Endocytosis of a2-Macroglobulin," *PNAS, USA* 79:2291–95 (1982) and Rikihisa et al., "Inhibition of Infection of Macrophages With Erlichia risticii by Cytochalasins, Monodansylcadaverine, and Taxol," *Infect. Immun.* 62:5126–32 (1994), which are hereby incorporated by reference). The HeLa cell monolayer was preincubated with the indicated concentrations of the compounds in MEM for 1 h (cytochalasin D) or 3 h (MDC) at 37° C. Mcep1-coated fluorescent latex beads, prepared as described above, were added to the monolayers. The preincubation with nocodazole was carried out at 4° C. (to bring about complete disassembly of the microtubules) with the indicated concentrations of the drug for 1 hr followed by incubation at 37° C. for 5 hrs. The compounds were maintained in the medium during the entire incubation periods with the beads. The cells were then washed with PBS and fixed with 100% methanol. Fluorescence emission per well (in fluorescence units/$10^5$ cells) was measured on Cytofluor reader. Each assay was conducted in triplicate and was independently repeated three times for each compound.

Example 7

Expression and Purification of the Recombinant Mcel Protein (rMcep1).

Upon induction with IPTG, *E. coli* BL21 (DE3) harboring pETmcel expressed large quantities of a protein of approximately 27 kDa (FIG. 1). The sequence analysis of the mce1 in the vector indicated that the expressed product was a fusion protein containing the pET23c vector-encoded sequences called the T7 tag at the N-terminus and a 37-amino acid peptide at the C-terminus. The N-terminus sequence analysis confirmed that the protein contained a 12 amino acid T7 tag sequence, followed by Val, Asn, Ala, Asp, Ile, which was identical to the N-terminus sequence deduced from mce1. *E. coli* M15(pREP4) containing pQEmcel expressed a protein of approximately 25 kDa, and its purification by the Ni-NTA resin column confirmed that it had a 6xHis tag at its N-terminus (date not shown).

Figure 1B:
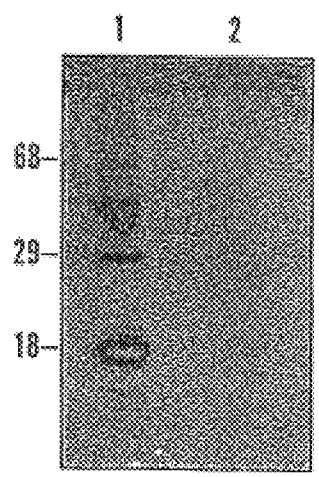
FIG. 1(B) is a silver stain of a 15% SDS-polyacrylamide gel which reveals the purified 27 kDa rMcel protein (approximately 1.5 mg). Lane 1 contains MW markers.

The recombinant mce1 product expressed in pET23mcel was purified to homogeneity, as observed in silver-stained SDS-PAGE gel (FIG. 1B). Protein concentrations of less than 0.3 mg/ml in PBS allowed it to remain in solution.

Example 8

The Native Mcep is Expressed on the Surface of *M. tuberculosis* Organism.

Figure 2A:
FIG. 2 is a colloidal gold immunoelectron microscopic analyses of *Mycobacterium tuberculosis* strain H37Ra. A 5-day growth of the bacteria was incubated with rabbit polyclonal anti-rMcep1 antibody followed by incubation with colloidal gold particles (5 nm) conjugated to anti-rabbit IgG antibody raised in goat (A). Electron dense gold particles decorate the surface of the 5-day growth of *M. tuberculosis*. A 3-week growth of the same strain of *M. tuberculosis* incubated with the antibody shows reduced labeling by the gold particles (B). A 5-day growth of the bacilli incubated with the same rabbit's pre-vaccination serum shows no binding of the gold particles (C). Bars=0.1 mm.
Figure 2B:
Figure 2C:
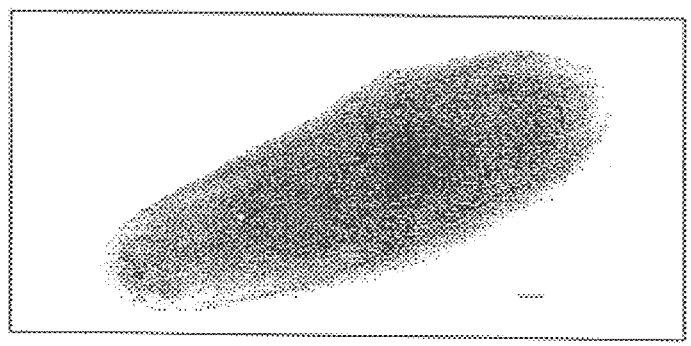

The electron dense colloidal gold particles were visible on the surface of the organism incubated with the polyclonal antibody raised against rMcep1, but not on the organism incubated with the same rabbit's prevaccination serus (FIG. 2). The number of colloidal gold particles on a 3-week growth of *M. tuberculosis* was considerably less than that on a 5-day growth, suggesting that the native Mcep may be expressed on the surface of the organism during log phase growth.

Example 9
The Antibody to rMcep1 Recognizes a Single Native *M. tuberculosis* Protein.

Figure 3:
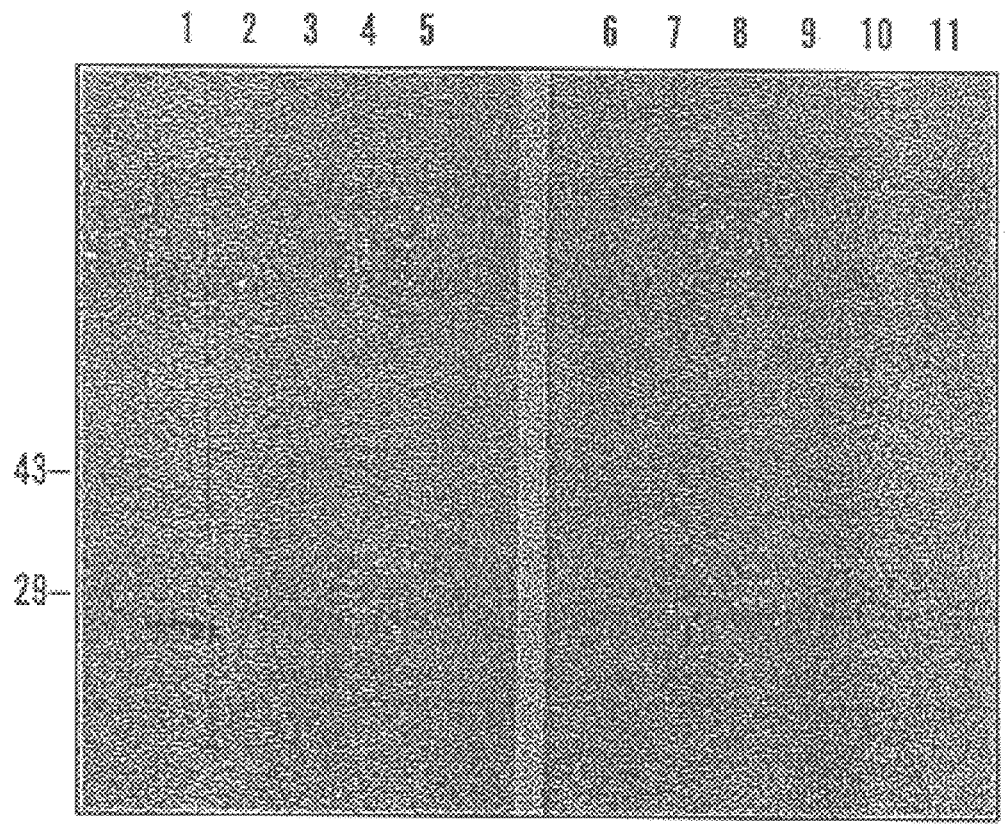
FIG. 3 is an immunoblot analysis of the recombinant Mcel protein and *M. tuberculosis* subcellular fractions. The anti-rMcep1 antibody recognizes a 45 kd protein in approximately 50 mg of the whole cell lysate (lane 2), and 5 mg each of the cell wall (lane 3), cell membrane (lane 4), and cytosol (lane 5) of the H37Ra strain. The cell wall and membrane fractions are enriched in the protein. The antibody detected the recombinant Mcep1 as a 27 kd protein (lane 1). Lane 6 contains pre-stained MW markers. Lanes 7–11 contain proteins corresponding to those in lanes 2–6, blotted with serum from the same rabbit obtained before it was immunized with rMcep1.

The anti-rMcep1 antibody recognized a protein of about 45 kDa from the subcellular fractions of an *M. tuberculosis* H37Ra strain (FIG. 3). The protein was most abundant in the cell wall and membrane fractions. The amino acid sequence analysis of the native protein recognized by the anti-rMcep1 antibody found it to be blocked at the N-terminus.

The sequence analysis of the 4.8 kb *M. tuberculosis* SauIIA DNA fragment containing mce1 showed that the 627-bp fragment was located within a region containing several potential open reading frames, one of which is predicted to encode a product of 45.5 kDa with an initiation codon GTG. The nucleotide sequence of this region has been deposited in the GenBank to update a previously-submitted sequence deposited under accession number X70901.

Example 10
rMcep1 Promotes Uptake of Protein-coated Latex Microspheres into HeLa Cells.

Figure 4A:
FIG. 4 is a transmission electron microscopy of HeLa cells incubated with rMcep1-coated polystyrene latex microspheres. HeLa cells were incubated with 1.1 mm latex beads for 5 hrs (A) and 24 hrs (B). The oval-shaped electron dense particles are internalized. No beads were visible inside cells incubated for 24 hrs with latex beads coated with bovine serum albumin (C) or *E. coli* BL21 lysate, truncated rMcep1, or an unrelated recombinant protein cloned from *M. tuberculosis* (not shown; see text). Bars=1 mm.
Figure 4B:
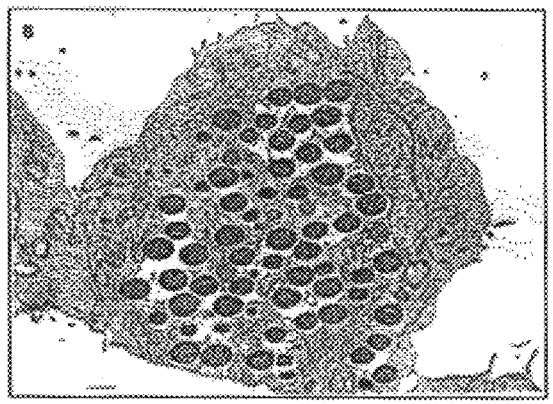
Figure 4C:
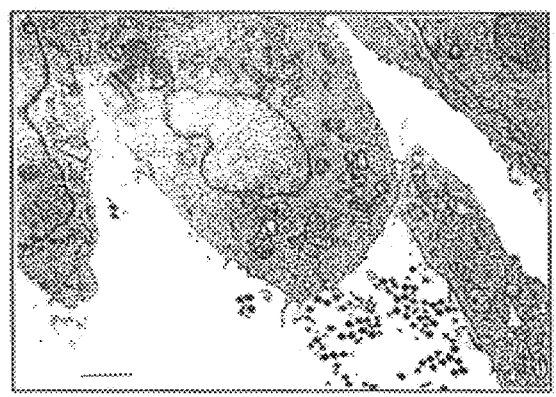

Light microscopy revealed that 0.3 mm and 1.1 mm-diameter beads coated with rMcep1 derived from pET23 mce1 or pQEmce1 readily associated with HeLa cells (data not shown). Electron microscopy confirmed that this association involved internalization of the beads into the cells (FIG. 4). The uptake of the beads was time dependent. The fluorescent emission determinations over time of rMcep1-coated 1.0 mm fluorescent beads (FIG. 5A) indicated progressive increase in the uptake of the beads. Uncoated beads, or beads coated with the *E. coli* (BL21) lysate, BSA, truncated rMcep1 (expressed by pQEmce2) (FIG. 5C), or an unrelated recombinant *M. tuberculosis* protein encoded by pQENO14 (which also has a 6xHis tag at its N-terminus; data not shown) did not enter HeLa cells even after 24 hrs. No differences in the uptake levels of beads coated with either pET23 or pQE vector-expressed rMcep1 were observed.

The solubilized protein blocked the uptake of the beads coated with 2.5 mg/ml concentration of rMcep1 in a dose-dependent manner (FIG. 5B). The uptake was also saturatable, where no further increase in uptake was demonstrable with the indicated number of beads coated with rMcep1 concentrations of >1 mg/ml incubated for 4 hrs with approximately $10^5$ cells (FIG. 5C).

Example 11
rMecp1 Promotes both Phagocytosis and Endocytosis in HeLa Cells.

The internalized beads were observed within vacuolar compartments (FIG. 4). Some vacuoles contained only one bead, while others contained multiple beads. No beads were observed to be free in the cytoplasm at 4 or 24 hrs.

Figure 6A:
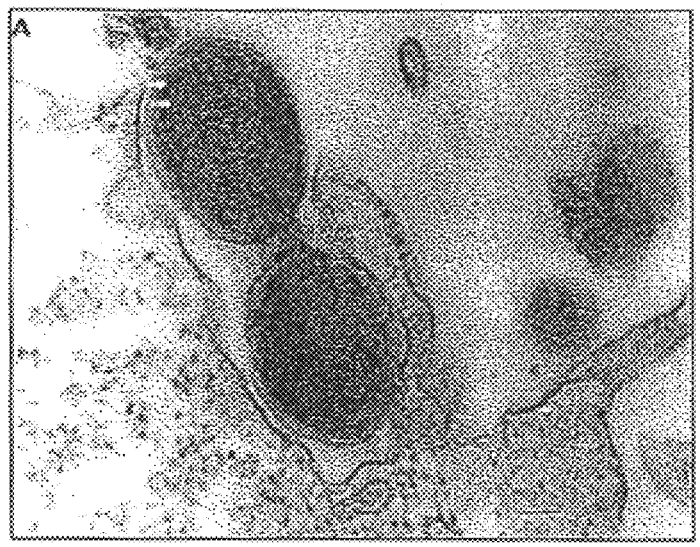
Figure 6B:
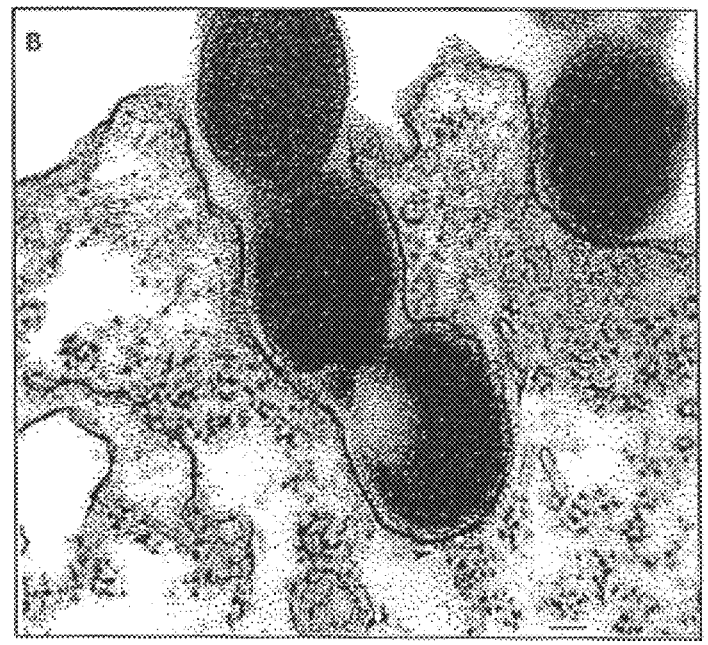

The rMcep1-coated beads at the plasma membrane surface of the cells elicited filopodia and pedestal formations, indicating microfilament rearrangement (FIG. 6A). Some of the beads in contact with the cell surface induced membrane invagination, thickening, and formation of a regular array of bristles resembling clathrin coats (FIG. 6B). These responses were not dependent on the diameter of the beads. Both 0.3 mm and 1.1 mm beads coated with rMcep1 elicited similar membrane surface responses.

To further support the electron microscopy morphologic evidence that both microfilament and microtubule rearrangement was involved in the uptake of rMcep-coated latex beads, HeLa cells were treated with cytochalasin D, nocodazole, and monodansylcadaverine (MDC). Cytochalasin D depolymerizes microfilaments, while nocodazole blocks microtubule assembly (Carter, S. B., "Effects of Cytochalasins on Mammalian Cells," *Nature* 213:261–4 (1967) and Parczyk et al., "Microtubules Are Involved in the Secretion of Proteins at the Apical Cell Surface of the Polarized Epithelial Cells, Madin-Darby Canine Kidney," *J. Biol. Chem.* 264:16837–46 (1989), which are hereby incorporated by reference). MDC has been shown to inhibit clathrin assembly during coated vesicle formation (Schlegel et al., "Amantadine and Dansylcadaverine Inhibit Vesicular Stomatitis Virus Uptake and Receptor-mediated Endocytosis of a2-Macroglobulin," *PNAS, USA* 79:2291–95 (1982), which is hereby incorporated by reference). Cytochalasin D at concentrations of 0.1–5 mg/ml blocked the association of the protein-coated beads in a dose-dependent manner, as revealed by fluorescence emission measurements of fluorescent latex beads coated with rMcep1 (FIG. 5D). However, the inhibition was not complete. Concentrations of cytochalasin D higher than 5 mg/ml caused HeLa cells to slough off the plate surface. Nocodazole also inhibited the association of the beads in a dose dependent fashion (FIG. 5E), but the inhibition was again not complete, even at 5 mg/ml. Concentrations higher than this were cytotoxic. The combination of both compounds at the lowest concentrations (0.1 mg/ml) was cytotoxic. MDC at concentrations of 1–100 mm partly inhibited the association (FIG. 5F).

The cellular uptake analyses in this study were performed with He-La cells which, of course, are not the natural target cells of *M tuberculosis*. The cells were used not to represent an in vivo infection process, but used to identify an *M. tuberculosis* product that promotes cytoskeletal rearrangement in mammalian cells. Because HeLa cells are not phagocytes, the entry of the latex beads into the cells can be unequivocally attributed to the effect of the recombinant mce 1 product. The dramatic cell membrane pertubations elicited by the protein indicate that it stimulates cytoskeletal rearrangement in HeLa cells, which clearly involves signal tranduction. The use of HeLa cells, therefore, facilitated identification of an *M. tuberculosis* product that induces signal transduction in mammalian cells. Such a protein may have an effect on macrophages that is distinct from or in addition to the effect on their cytoskeletons.

For example, invasin, a *Yersinia pseudotuberculosis* protein initially reported to mediate the organism's uptake into HEp-2 cells (nonphagocytic cells), was recently shown to inhibit the induction of oxidative burst activity by murine macrophages during phagocytosis (Bliska et al., "Inhibition of the Fc Receptor-mediated Oxidative Burst in Macrophages by the *Yersinia pseudotuberculosis* Tyrosine Phosphatase," *Infect. Immun.* 63:681–85 (1995), which is hereby incorporated by reference). rMcep1 may influence the early signaling events during phagocytosis by macrophages that determine the bacilli's intracellular fate. The present work lays a groundwork for studies to examine the signal activation in macrophages by rMcep1, and its effect on *M. tuberculosis* survival.

These observations show that the mce 1 product promotes uptake into mammalian cells of inert, synthetic particles by phagocytosis and receptor-mediated endocytosis. The failure of HeLa cells to take up beads coated with BSA, *E. coli* lysate, truncated rMcep1, or an unrelated *M. tuberculosis* recombinant protein suggests that this interaction is induced by rMcep1 alone. It was shown previously that the 5' region of the putative open reading frame comprising mce 1 was important for the cell uptake activity (Arruda et al., "Cloning of an *M. tuberculosis* DNA Fragment Associated With Entry and Survival Inside Cells," *Science* 261:1454–57 (1993), which is hereby incorporated by reference); this was confirmed by the failure of an N-terminus-truncated rMcep1 (rMcep2) to deliver beads into HeLa cells (FIG. 5C).

The native protein recognized by an antibody raised against rMcep1 was noted to have a MW (~45 kDa) different from that of rMcep1 (27 kDa or 25 kDa). Most likely, this is because the 627-bp sequence is part of a larger open reading frame in the native *M. tuberculosis* chromosome. It should be noted that the sequence downstream of the native mce 1 region is not the same as that observed in the corresponding downstream region in the originally cloned 1535-bp DNA fragment (Arruda et al., "Cloning of an *M. tuberculosis* DNA Fragment Associated With Entry and Survival Inside Cells," *Science* 261:1454–57 (1993), which is hereby incorporated by reference). In the 1535-bp fragment, there are 2 SauIIA sites immediately downstream and upstream of the 627-bp fragment. The 627-bp fragment may have been scrambled into these sites during the initial genomic library construction. The sequences flanking the 627-bp fragment in the newly-cloned 4.8 kb segment are different from those in the corresponding region in the 1535-bp fragment. These flanking sequences were confirmed to be identical in *M. tuberculosis* strain H37Ra and in a clinical strain (CB3.3) of *M. tuberculosis*. Hence, the mce 1 product rMcep1 appears to be a truncated but yet biologically active protein. The native Mcep is now undergoing purification.

The ability of the soluble protein to competitively inhibit the association of the rMcep1-coated beads and the observation that this association was saturated with increasing concentrations of the protein on the beads, suggest that this interaction is a receptor-mediated process. Since the phagocytic uptake of *M. tuberculosis* into monocyte derived macrophages can be partly blocked by monoclonal antibodies to complement receptors (CR1, 3, and 4) as well as to the mannose receptors (Schlesinger et al., "Phagocytosis of *Mycobacterium tuberculosis* is Mediated By Human Monocyte Complement Receptors and Complement Component C3," *J. Immunol.* 144:2771–80 (1990); Schlesinger et al., "Macrophage Phagocytosis of Virulent But Not Attenuated Strains of *Mycobacterium tuberculosis* is Mediated by Mannose Receptors in Addition to Complement Receptors," *J. Immunol.* 150:2920–30 (1993); and Hirsch et al., "Complement Receptor-mediated Uptake and Tumor Necrosis Factor-alpha-mediated Growth Inhibition of *Mycobacterium tuberculosis* by Human Alveolar Macrophages," *J. Immunol.* 152:743–53 (1994), which are hereby incorporated by reference), if rMcep1-promoted entry is a receptor-mediated process, this organism appears to have evolved to exploit a variety of membrane receptor-mediated pathways to enter cells.

Both transmission electron microscopic studies and cytoskeleton polymerization inhibition studies provide evidence that the entry into HeLa cells of rMcep1-coated latex beads involves microfilament and microtubule rearrangement. To distinguish endocytosis mediated by coated versus non-coated vesicle pathways, MDC, a tranglutaminase inhibitor known to block clustering of ligand-receptor complexes into clathrin-coated vesicles (Schlegel et al., "Amantadine and Dansylcadaverine Inhibit Vesicular Stomatitis Virus Uptake and Receptor-mediated Endocytosis of a2-Macroglobulin," *PNAS. USA* 79:2291–95 (1982) and Rikihisa et al., "Inhibition of Infection of Macrophages With Erlichia risticii by Cytochalasins, Monodansylcadaverine, and Taxol," *Infect. Immun.* 62:5126–32 (1994), which are hereby incorporated by reference) was used. The negative effect on cell association by MDC indicates that rMcep1 triggers coated vesicle-mediated endocytosis, which was confirmed by the electron microscopy observation of coated vesicles in association with rMcep1-coated microspheres (FIG. 6B). Since HeLa cells themselves are not phagocytes, it is concluded that the protein itself stimulates signal transduction pathways linked to mammalian cytoskeletal networks that mediate phagocytosis and endocytosis.

The colloidal gold immunoelectron microscopy studies suggest that the native Mcep is expressed on the surface of *M. tuberculosis* (FIG. 2). Bacilli after 5 days of growth expressed more of the protein than bacilli examined at their stationary phase of growth (>3 weeks). This observation is consistent with the pathogenic process of *M. tuberculosis* infection, in which the protein may be induced during the early proliferative phase of infection but not after the organism establishes itself inside a cell. *M. tuberculosis* entry into human lung epithelial cells in culture was recently reported to be enhanced if the bacteria were first passaged through macrophages (McDonough et al., "Cytotoxicity for Lung Epithelial Cells is a Virulence-associated Phenotype of *Mycobacterium tuberculosis*," *Infect. Immun.* 63:4802–11 (1995), which is hereby incorporated by reference), and Mcep may play such a role.

Mcep, expressed on the surface of the organism, clearly has a target outside of the tubercle bacillus itself, this characteristic satisfies a major condition that this protein is a virulence determinant of *M. tuberculosis*. Such a determinant may serve as a potential vaccine candidate against tuberculosis.

Although the invention has been described in detail for the purpose of illustration, it is understood that such detail is solely for that purpose, and variations can be made therein by those skilled in the art without departing from the spirit and scope of the invention which is defined by the following claims.

SEQUENCE LISTING

```
<160> NUMBER OF SEQ ID NOS: 2

<210> SEQ ID NO 1
<211> LENGTH: 1584
<212> TYPE: DNA
<213> ORGANISM: Mycobacterium tuberculosis
```

-continued

```
<400> SEQUENCE: 1 atgtctttttg gtccttcttg gaggccctca tcatcactgc gatcgtcatg g tcagccact      60
gctactacgg gtacgccgcc ggtggaggcc ccgtcggtgt cggcgaggcc g tcggccgat     120
cgatgcgttt ctcgttggtc tcggtgcagg tcgttgtcct gtttgcagcg t tggcgctct     180
acggtgtcga cccgaacttc aatctcacgg tgtagccgca tgacgacgcc g gggaagctg     240
aacaaggcgc gagtgccgcc ctacaagacg gcgggtttgg gtctagtgct g gtcttcgcg     300
ctcgtagttg ccttggtata cctgcagttt cgcggggagt tcacgcccaa g acgcagttg     360
acgatgctgt ccgctcgtgc gggtttggtg atggatcccg ggtcgaaggt c acctataac     420
ggggtggaga tcgggcgggt agacaccatc tcggaggtca cacgtgacgg c gagtcggcg     480
gccaagttca tcttggatgt ggatccgcgt tacatccacc tgattccggc a atgtgaac      540
gccgacatca aggcgaccac ggtgttcggc ggtaagtatg tgtcgttgac c acgccgaaa     600
aacccgacaa agaggcggat aacgccaaaa gacgtcatcg acgtacggtc g gtgaccacc     660
gagatcaaca cgttgttcca gacgctcacc tcgatcgccg agaaggtgga t ccggtcaag     720
ctgaacctga ccctgagcgc ggccgcggag gcgttgaccg ggctgggcga t aagttcggc     780
gagtcgatcg tcaacgccaa caccgttctg gatgacctca attcgcggat g ccgcagtcg     840
cgccacgaca ttcagcaatt ggcggctctg gcgacgtct acgccgacgc g gcgccggac     900
ctgttcgact ttctcgacag ttcggtgacc accgcccgca ccatcaatgc c cagcaagcg     960
gaactggatt cggcgctgtt ggcggcggcc gggttcggca caccacagc c gatgtcttc    1020
gaccgcggcg ggccgtatct gcagcggggg gtcgccgacc tggtcccac c gccaccctg    1080
ctcgacactt atagcccgga actgttctgc acgatccgca acttctacga t gccgatccg    1140
ctcgctaaag cggcgtccgg tggcggtaac ggctactcgc tgaggacgaa c tcagagatc    1200
ctatccggga taggtatctc cttgttgtct ccctggcgt tagccaccaa t ggggcggca    1260
atcggaatcg gactggtagc cggattgata cgccgcccc tcgcggtggc c gcaaatcta    1320
gcgggagccc tacccggaat cgttggcggc gcgcccaatc cctataccta t ccggagaat    1380
ctgccgcggg tgaacgctcg cggtggcccg gggggcgccc ccggttgctg g cagccgatc    1440
acccgggatc tgtggccagc gccgtatctg gtgatggaca ccggtgccag c ctcgccccg    1500
tacaaccaca tggaggttgg ctcgccttat gcagtcgagt acgtctgggg c cgtcaggta    1560
ggggataaca cgatcaaccc atga                                            1584

<210> SEQ ID NO 2
<211> LENGTH: 527
<212> TYPE: PRT
<213> ORGANISM: Mycobacterium tuberculosis

<400> SEQUENCE: 2

Met Ser Phe Gly Pro Ser Trp Arg Pro Ser S er Ser Leu Arg Ser Ser
 1               5                  10                  15

Trp Ser Ala Thr Ala Thr Thr Gly Thr Pro P ro Val Glu Ala Pro Ser
            20                  25                  30

Val Ser Ala Arg Pro Ser Ala Asp Arg Cys V al Ser Arg Trp Ser Arg
        35                  40                  45

Cys Arg Ser Leu Ser Cys Leu Gln Arg Trp A rg Ser Thr Val Ser Thr
    50                  55                  60

Arg Thr Ser Ile Ser Arg Cys Ser Arg Met T hr Thr Pro Gly Lys Leu
65                  70                  75                  80
```

-continued

```
Asn Lys Ala Arg Val Pro Pro Tyr Lys Thr Ala Gly Leu Gly Leu Val
                85                  90                  95

Leu Val Phe Ala Leu Val Ala Leu Val Tyr Leu Gln Phe Arg Gly
            100                 105                 110

Glu Phe Thr Pro Lys Thr Gln Leu Thr Met Leu Ser Ala Arg Ala Gly
            115                 120                 125

Leu Val Met Asp Pro Gly Ser Lys Val Thr Tyr Asn Gly Val Glu Ile
130                 135                 140

Gly Arg Val Asp Thr Ile Ser Glu Val Thr Arg Asp Gly Glu Ser Ala
145                 150                 155                 160

Ala Lys Phe Ile Leu Asp Val Asp Pro Arg Tyr Ile His Leu Ile Pro
                165                 170                 175

Ala Asn Val Asn Ala Asp Ile Lys Ala Thr Thr Val Phe Gly Gly Lys
            180                 185                 190

Tyr Val Ser Leu Thr Thr Pro Lys Asn Pro Thr Lys Arg Arg Ile Thr
            195                 200                 205

Pro Lys Asp Val Ile Asp Val Arg Ser Val Thr Thr Glu Ile Asn Thr
210                 215                 220

Leu Phe Gln Thr Leu Thr Ser Ile Ala Glu Lys Val Asp Pro Val Lys
225                 230                 235                 240

Leu Asn Leu Thr Leu Ser Ala Ala Glu Ala Leu Thr Gly Leu Gly
                245                 250                 255

Asp Lys Phe Gly Glu Ser Ile Val Asn Ala Asn Thr Val Leu Asp Asp
            260                 265                 270

Leu Asn Ser Arg Met Pro Gln Ser Arg His Asp Ile Gln Gln Leu Ala
            275                 280                 285

Ala Leu Gly Asp Val Tyr Ala Asp Ala Ala Pro Asp Leu Phe Asp Phe
            290                 295                 300

Leu Asp Ser Ser Val Thr Thr Ala Arg Thr Ile Asn Ala Gln Gln Ala
305                 310                 315                 320

Glu Leu Asp Ser Ala Leu Leu Ala Ala Ala Gly Phe Gly Asn Thr Thr
                325                 330                 335

Ala Asp Val Phe Asp Arg Gly Gly Pro Tyr Leu Gln Arg Gly Val Ala
            340                 345                 350

Asp Leu Val Pro Thr Ala Thr Leu Leu Asp Thr Tyr Ser Pro Glu Leu
            355                 360                 365

Phe Cys Thr Ile Arg Asn Phe Tyr Asp Ala Asp Pro Leu Ala Lys Ala
370                 375                 380

Ala Ser Gly Gly Gly Asn Gly Tyr Ser Leu Arg Thr Asn Ser Glu Ile
385                 390                 395                 400

Leu Ser Gly Ile Gly Ile Ser Leu Leu Ser Pro Leu Ala Leu Ala Thr
                405                 410                 415

Asn Gly Ala Ala Ile Gly Ile Gly Leu Val Ala Gly Leu Ile Ala Pro
            420                 425                 430

Pro Leu Ala Val Ala Ala Asn Leu Ala Gly Ala Leu Pro Gly Ile Val
            435                 440                 445

Gly Gly Ala Pro Asn Pro Tyr Thr Tyr Pro Glu Asn Leu Pro Arg Val
450                 455                 460

Asn Ala Arg Gly Gly Pro Gly Gly Ala Pro Gly Cys Trp Gln Pro Ile
465                 470                 475                 480

Thr Arg Asp Leu Trp Pro Ala Pro Tyr Leu Val Met Asp Thr Gly Ala
                485                 490                 495
```

-continued

```
Ser Leu Ala Pro Tyr Asn His Met Glu Val G ly Ser Pro Tyr Ala Val
            500                 505                 510

Glu Tyr Val Trp Gly Arg Gln Val Gly Asp A sn Thr Ile Asn Pro
            515                 520                 525
```

What is claimed:

1. An isolated protein or polypeptide encoded by a DNA molecule which confers on *Mycobacterium tuberculosis* an ability to enter mammalian cells, wherein said protein or polypeptide has an amino acid sequence selected from the group consisting of an amino acid sequence having SEQ. ID. No. 2, an amino acid sequence comprising amino acid 1 to amino acid 167 of SEQ. ID. No. 2, an amino acid sequence comprising amino acid 95 to amino acid 167 of SEQ. ID. No. 2, an amino acid sequence comprising amino acid 95 to amino acid 527 of SEQ. ID. No. 2, and an amino acid sequence comprising amino acid 379 to amino acid 527 of SEQ. ID. No. 2.

2. An isolated protein or polypeptide according to claim 1, wherein said protein or polypeptide has an amino acid sequence having SEQ. ID. No. 2.

3. An isolated protein or polypeptide according to claim 1, wherein said protein or polypeptide has an amino acid sequence comprising amino acid 1 to amino acid 167 of SEQ. ID. No. 2.

4. An isolated protein or polypeptide according to claim 1, wherein said protein or polypeptide has an amino acid sequence comprising amino acid 95 to amino acid 167 of SEQ. ID. No. 2.

5. An isolated protein or polypeptide according to claim 1, wherein said protein or polypeptide has an amino acid sequence comprising amino acid 95 to amino acid 527 of SEQ. ID. No. 2.

6. An isolated protein or polypeptide according to claim 5, wherein said protein or polypeptide has a molecular weight of about 45 kDa.

7. An isolated protein or polypeptide according to claim 1, wherein said protein or polypeptide has an amino acid sequence comprising amino acid 379 to amino acid 527 of SEQ. ID. No. 2.

8. An isolated protein or polypeptide according to claim 1, wherein said protein or polypeptide is recombinant.

9. An isolated protein or polypeptide according to claim 1, wherein said protein or polypeptide is purified.

* * * * *

UNITED STATES PATENT AND TRADEMARK OFFICE
CERTIFICATE OF CORRECTION

PATENT NO. : 6,399,764 B1
APPLICATION NO. : 09/574462
DATED : June 4, 2002
INVENTOR(S) : Lee W. Riley It is certified that error appears in the above-identified patent and that said Letters Patent is hereby corrected as shown below:

Col. 1 at lines 10-12, delete "This invention was developed with government funding under National Institutes of Health Grant No. RO1 AI35266. The U.S. Government may have certain rights in this invention." and insert --This invention was made with government support under grant RO1 AI35266 awarded by National Institutes of Health. The government has certain rights in the invention-- in its place.

Signed and Sealed this

Third Day of March, 2009

JOHN DOLL
*Acting Director of the United States Patent and Trademark Office*